United States Patent [19]

Wuts

[11] Patent Number: 5,430,176
[45] Date of Patent: Jul. 4, 1995

[54] INTERMEDIATE USEDF FOR THE PREPARATION OF DEFEROXAMINE

[75] Inventor: Peter G. M. Wuts, Kalamazoo, Mich.

[73] Assignee: The Upjohn Company, Kalamazoo, Mich.

[21] Appl. No.: 199,038

[22] Filed: Feb. 18, 1994

Related U.S. Application Data

[60] Division of Ser. No. 999,486, Dec. 30, 1992, abandoned, which is a continuation-in-part of Ser. No. 649,864, Feb. 4, 1991, abandoned, which is a continuation-in-part of Ser. No. 548,717, Jul. 6, 1990, Pat. No. 5,011,976.

[51] Int. Cl.$^6$ ............................................. C07C 269/06
[52] U.S. Cl. ............................................. 560/159
[58] Field of Search .................. 560/32, 31, 161, 163, 560/159

[56] References Cited

U.S. PATENT DOCUMENTS

| | | | |
|---|---|---|---|
| 3,118,823 | 1/1964 | Gaeumann et al. | 195/80 |
| 3,153,621 | 10/1964 | Gaeumann et al. | 195/80 |
| 3,158,552 | 11/1964 | Gaeumann et al. | 195/80 |
| 3,247,197 | 4/1966 | Gaeumann et al. | 260/244 |
| 3,471,476 | 10/1969 | Gaeumann et al. | 260/239.3 |
| 3,576,844 | 4/1971 | Ishida et al. | 560/159 |
| 3,898,271 | 8/1975 | Sheehan et al. | 260/473 R |
| 3,914,300 | 10/1975 | Haddock et al. | 260/553 A |
| 4,028,398 | 6/1977 | Satzinger et al. | 260/471 A |
| 4,987,253 | 1/1991 | Bergler | 562/623 |
| 5,039,672 | 8/1991 | Eggler et al. | 514/210 |
| 5,124,455 | 6/1992 | Lombardo | 546/181 |

FOREIGN PATENT DOCUMENTS 0347163 12/1989 European Pat. Off. .

OTHER PUBLICATIONS

March, "Advanced Organic Chemistry," 3rd ed., John Wiley & Sons, New York (1985), pp. 805–806.

H. Bickel et al., "Soffwechselprodukte von Actinomyceten, Uber die Konstitution von Ferrioxamin B," Helv. Chim. Acta 43:2129–38 (1960).

Prelog, V. and A. Walser, "Stoffwechselprodukte von Actinomyceten, Uber die Synthese der Ferrioxamine B and D$_1$, "Helv. Chim. Acta 45:631–37 (1962).

Bergeron, R. J. and J. J. Pegram, "An Efficient Total Synthesis of Desferrioxamine B," 53(14):3131–3134 (1988).

Primary Examiner—José G. Dees
Assistant Examiner—Barbara S. Frazier
Attorney, Agent, or Firm—Donald L. Corneglio

[57] ABSTRACT

A method for preparing deferoxamine and a composition of Formula I $$X-Ph-CH_2-O-C(O)-NH-(CH_2)_4-CH=NOR$$

wherein X is a $C_1-C_4$ alkyl, $-O(C_1-C_4 alkyl)$, a halogen or hydrogen,; R is $X-Ph-CH_2-$ or hydrogen for preparing deferoxamine. In one embodiment X and R are hydrogen. The intermediate, Formula I, has the advantage of being prepared in fewer and more efficient steps from readily available materials than conventional means for preparing deferoxamine.

3 Claims, No Drawings

INTERMEDIATE USEDF FOR THE PREPARATION OF DEFEROXAMINE

CROSS-REFERENCE TO RELATED APPLICATIONS

This application is a divisional of U.S. Ser. No. 07/999,486, filed Dec. 30, 1992, now abandoned, which was the national phase of PCT application no. PCT/US91/04339; which is a continuation-in-part of U.S. Ser. No. 07/649,864, filed 4 Feb. 1991, abandoned; which is a continuation-in-part of U.S. Ser. No. 07/548,717, filed 6 Jul. 1990, issued 30 Apr. 1991, U.S. Pat. No. 5,011,976.

BACKGROUND OF THE INVENTION

The present invention is directed toward a novel, key intermediate useful for the preparation of deferoxamine. Deferoxamine is well known in the art as a natural product which is a microbial iron chelator and was first isolate from *Streptomyces pilosus* which utilized it to obtain iron from the environment. Its synthesis and characterization were documented by Bickel (Helv. Chim. Acta. Vol.43. p. 2129) in 1960. Deferoxamine has various pharmaceutical uses such as the treatment of hemodialysis-induced aluminum accumulation in the brain and for iron overload conditions.

The synthesis of deferoxamine and its analogs has been described in various publications such as U.S. Pat. Nos. 3,471,476 and 3,247,197 and European Patent Application 0 347 163 published 20 Dec. 1989. Despite the various methods disclosed for the synthesis of deferoxamine new and more economical means for synthesis have been sought. The present invention discloses a key intermediate which can be prepared from readily available ingredients and using conventional chemistry. This provides a distinct advantage over previous methods for the synthesis of deferoxamine which have required the use sensitive chemical procedures or difficult to prepare intermediates.

INFORMATION DISCLOSURE STATEMENT

Various synthesis methods for preparing deferoxamine are described in publications such as Bickel, *Helv. Chim. Acta.*, 43 2129 (1960); *Helv. Chim. Acta.*, 45 631 (1962); and R. J. Bergeron and J. J. Pegram, *J. Org. Chem.*, 53 3131 (1988).

U.S. Pat. Nos. 3,118,823; 3,153,621; 3,158,552; 3,247,197 and 3,471,476 describe the general state of the art with respect to deferoxamine. The latter two deal with the chemical synthesis of deferoxamine. European Patent Application publication to the University of Florida publication number 0 347 163 also describes the chemistry of deferoxamine similar to that of Bergeron.

SUMMARY OF THE INVENTION

In one aspect, the subject invention is an intermediate useful in the preparation of deferoxamine having Formula I

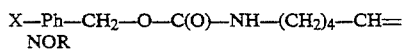

wherein X is a $C_1$-$C_4$ alkyl, —O($C_1$-$C_4$ alkyl), a halogen or hydrogen; R is X—Ph—$CH_2$— or hydrogen. In one preferred embodiment X and R are independently hydrogen or X is a methyl or methoxy group. In another preferred embodiment X and R are hydrogen. The intermediate has the advantage of being prepared in fewer and more efficient steps from readily available materials than conventional means for preparing deferoxamine.

In another aspect, the subject invention is the use of a compound of Formula I

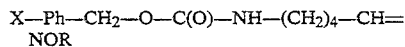

wherein X is a $C_1$-$C_4$ alkyl, —O($C_1$-$C_4$ alkyl), a halogen or hydrogen, and R is X—PH—$CH_2$— or hydrogen for preparing deferoxamine. The use comprises the steps of (a) reacting an oxime compound of Formula I to form a hydroxylamine; (b) reacting the hydroxylamine to form amides of formula 9:ZN(H)—$(CH_2)_4$—CHN(OH)Ac and formula 8:ZN(H)—$(CH_5)_2$—N(OH)—C(O)—$(CH_2)_2$—C(O)—OH (where Z is a protecting group, preferably, —C(O)O$CH_2$Ph); (c) reacting formula 8 with a chloroformate and base to form an anhydride; and (d) reacting said anhydride with an amine derived from formula 9 to yield a coupled product of Formula II:ZN(H)—$(CH_2)_5$—N(OH)—C(O)—$(CH_2)_2$C(O)—N(H)—$(CH_2)_5$—N(OH)Ac; (e) reacting an amine derived from Formula II with said anhydride to give a Z protected deferoxamine.

In yet another aspect, the present invention is directed toward a method for preparing an oxime intermediate of Formula I: X—Ph—$CH_2$—O—C(O)—NH—$(CH_2)_4$—CH=NOR wherein X is a $C_1$-$C_4$ alkyl, —O($C_1$-$C_4$ alkyl), a halogen or hydrogen, R is X—PH—$CH_2$— or hydrogen. The method comprises the steps of (a) reacting a compound structurally represented by formula 11:

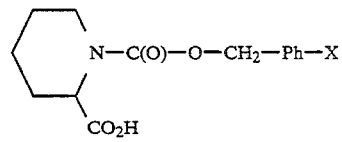

under electrolysis with a $C_1$-$C_4$ alcohol to form a compound structurally represented by formula 13.

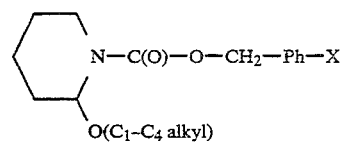

(b) treating said formula 13 with a hydroxylamine hydrochloride in pyridine or a $C_{1-4}$ alkyl substituted pyridine. The method can include in step (b) the addition of a $C_{1-4}$ alcohol, triethylamine or combination thereof. Preferably, formula 13 is converted to the oxime intermediate of Formula I by treatment with a hydroxylamine hydrochloride in pyridine and methyl alcohol.

DETAILED DESCRIPTION OF THE INVENTION

The present invention is directed toward a key intermediate for the preparation of deferoxamine (also referred to as desferrioxamine). Desferrioxamine B (12 in Schemes, below) is an excellent chelator for iron ($K_f = 10^{30}$ $M^{-1}$) and is used to treat diseases such as thalassemias. The intermediate is shown as Formula I:

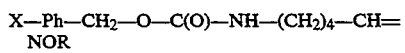
NOR wherein "X" is a $C_1$-$C_4$ alkyl, —O($C_1$-$C_4$ alkyl), a halogen (Cl, Br, F or I) or hydrogen any of which can be located at any of the positions on the phenyl ring (Ph); and where "R" is X—Ph—$CH_2$— or hydrogen.

A "$C_1$-$C_4$ alkyl" is methyl, ethyl, propyl or butyl including isomeric forms thereof. Methyl is a preferred alkyl. A "$C_{1-4}$ alcohol" is methyl, ethyl, propyl or butyl alcohol including isomeric forms thereof. A preferred intermediate is where X and R are individually or simultaneously hydrogen which would be 1-carbobenzoxyamino-5-hydroxyliminopentane 6.

The subject intermediate is shown in Scheme I and II as oxime 6. It can be used to prepare the siderophore desferrioxamine 12. In the Schemes, Z is a protecting group well known to those skilled in the art of organic synthesis for preventing reaction at a particular site of a chemical compound. A preferred protecting group is —C(O)OCH$_2$Ph.

Desferrioxamine was prepared from the subject intermediate oxime 6 as outlined in the Scheme I. The oxime can also be prepared as outlined in scheme II. While the electrolysis reaction is not new the conversion of the amide to the oxime is new, i.e. reacting formula 13 with hydroxylamine to form oxime 6. The sequence differs from that in Scheme I by replacement of the OH with an O-methyl group. Subsequent transformations of the oxime to the amides 8 and 9, where Z is a protecting group —C(O)OCH$_2$Ph, proceed via generally recognized methodology. The conversion of the hydroxamic acid 8 to the cyclic mixed anhydride 10 has been done with DCC or acetic anhydride as coupling agents. The conversion also proceeds with diisopropylcarbodiimide (DIC) or with a hindered acid chloride in the presence of base to form the cyclic mixed anhydride which is then used in the coupling steps. The use of DIC is an extension of the use of DCC. Another excellent means for forming the cyclic mixed anhydride is with isobutylchloroformate or the common variants of this reagent.

Preparation of Intermediate, Oxime (6)

A solution of piperidine 60 ml, acetic acid 51 ml and water 50 ml was prepared. This solution was then added to a slurry of Ca(OCl)$_2$, 150 ml MTBE (methyl t-butyl ether) and 75 ml of water keeping the temperature between 0° and 10° C. When the addition is complete the solution was stirred for an additional 20 minutes. The chloramine was then isolated with MTBE (2×150 mL). The combined MTBE layers were concentrated to 110 ml and this solution was slowly added to a slurry of 45 g of KOH in 100 ml of MeOH keeping the temperature between 20° and 27° C. Potassium chloride precipitates from the mixture. The mixture is kept at room temperature overnight and then treated with 150 ml of saturated NaHCO$_3$. The BnOC(O)Cl is slowly added. The pH starts at about 14 and slowly drops as the BnOC(O)Cl is added. When the pH reaches 9. 50% NaOH is added to keep it between 9 and 10. When the addition is complete stir the solution for 1 or more hours and then extract with 3×100 mL of MTBE. The combined MTBE layers were dried over magnesium sulfate, filtered and concentrated to a pale yellow oil. The crude amide is taken up in 200 ml or MeOH and 100 ml of pyridine and treated with 44 g of hydroxylamine hydrochloride at reflux for 4 hours. MeOH was distilled from the mixture. After cooling the solution to ~35° C., 400 ml of water was slowly added to knock out the oxime. The crystals were washed with water and MTBE and then dried with nitrogen to afford 69 g. of oxime, 48% yield. In general the yield of this reaction varies between about 45–65%. It should be noted that the initial conversion to the chloramine is not limited by the reaction described and that there are a number of other methods that can be used to accomplish this transformation.

The subject intermediate is prepared in efficient steps described above from readily available materials and represents an economical means for preparing deferoxamine. The final step as outlined above describes the use of hydroxylamine hydrochloride in pyridine and methyl alcohol however other embodiments can include the use of pyridine alone or its $C_{1-4}$ substituted forms thereof such as methyl pyridine or dimethyl pyridine. Typically, in order to avoid using large quantities of the pyridine or substituted pyridine a solvent such as a $C_{1-4}$ alcohol, triethylamine or combination thereof is used.

Scheme I

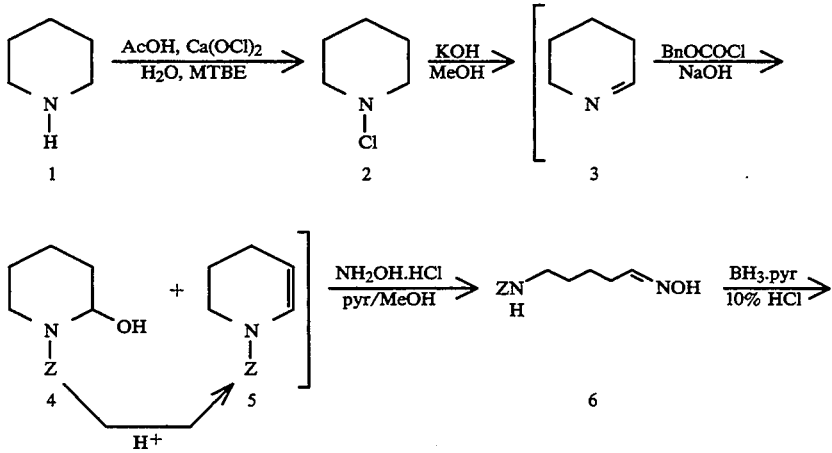

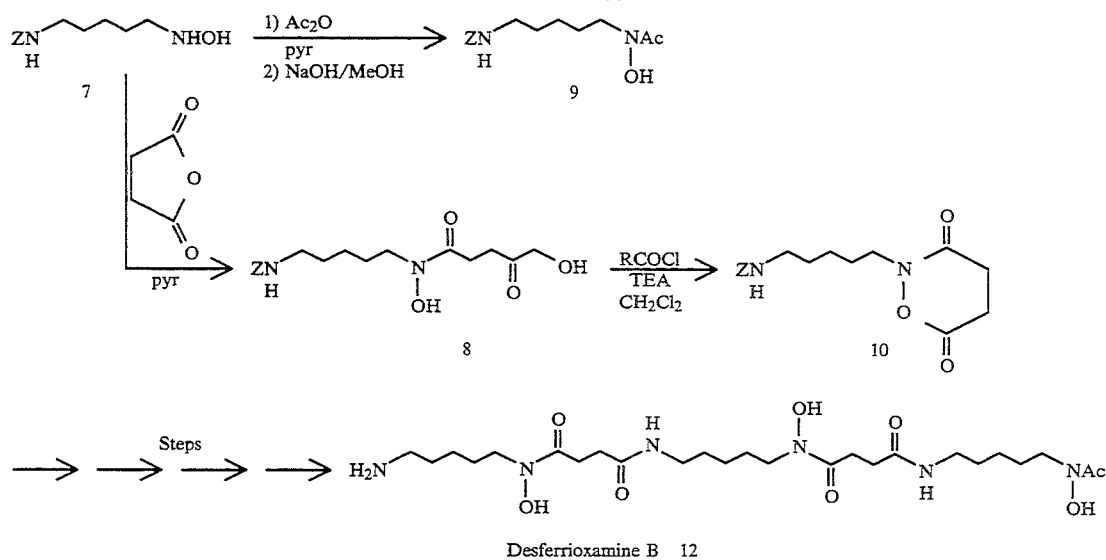

Desferrioxamine B  12

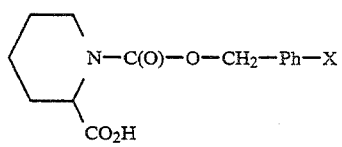

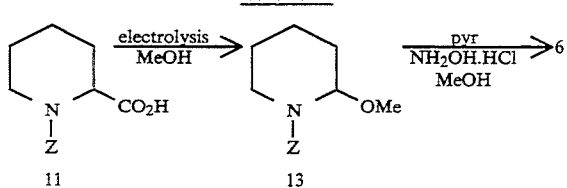

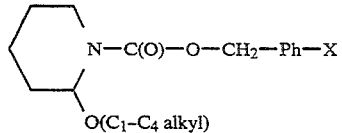

What is claimed:

1. A method for preparing an oxime intermediate of Formula I $$X\text{—}Ph\text{—}CH_2\text{—}O\text{—}C(O)\text{—}NH\text{—}(CH_2)_4\text{—}CH=NOR \quad \text{I}$$

wherein X is a $C_1$-$C_4$ alkyl, —$O(C_1$-$C_4$ alkyl), a halogen or hydrogen, hydrogen, comprising:

(a) reacting a compound structurally represented by formula 11 under electrolysis with a $C_1$-$C_4$ alcohol to form a compound structurally represented by formula 13

(b) treating said formula 13 with a hydroxylamine hydrochloride in pyridine or a $C_{1-4}$ alkyl substituted pyridine.

2. The method of claim 1 wherein said step (b) includes the addition of a of $C_{1-4}$ alcohol, triethylamine or combination thereof.

3. The method of claim 1 wherein said formula 13 is converted to said oxime intermediate of Formula I by treatment with a hydroxylamine hydrochloride in pyridine and methyl alcohol.

* * * * *